United States Patent
Sheng

(10) Patent No.: US 10,857,386 B2
(45) Date of Patent: Dec. 8, 2020

(54) SYSTEM AND METHOD FOR VOLUMETRIC MODULATED ARC THERAPY

(71) Applicant: The Regents of the University of California, Oakland, CA (US)

(72) Inventor: Ke Sheng, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 122 days.

(21) Appl. No.: 15/941,112

(22) Filed: Mar. 30, 2018

(65) Prior Publication Data

US 2018/0280725 A1     Oct. 4, 2018

Related U.S. Application Data

(60) Provisional application No. 62/479,296, filed on Mar. 30, 2017.

(51) Int. Cl.
*A61N 5/10* (2006.01)

(52) U.S. Cl.
CPC ......... *A61N 5/1047* (2013.01); *A61N 5/1031* (2013.01); *A61N 5/1039* (2013.01); *A61N 5/1065* (2013.01); *A61N 5/1081* (2013.01); *A61N 2005/1035* (2013.01)

(58) Field of Classification Search
CPC .. A61N 5/1031; A61N 5/1039; A61N 5/1047; A61N 5/1081; A61N 2005/1035; A61N 5/1065; A61N 5/1082
See application file for complete search history.

(56) References Cited

U.S. PATENT DOCUMENTS

| | | | |
|---|---|---|---|
| 9,764,162 B1* | 9/2017 | Willcut | A61B 5/743 |
| 2012/0136194 A1* | 5/2012 | Zhang | A61N 5/103 |
| | | | 600/1 |

OTHER PUBLICATIONS

Bedford J.L., "Treatment planning for volumetric modulated arc therapy," Med. Phys. 36, 5128-5138 (2009).
Bortfeld et al, "Single-arc IMRT?," Phys. Med. Biol. 54, N9-N20 (2009).
Bratengeier K., "2-Step IMAT and 2-Step IMRT in three dimensions," Med. Phys. 32, 3849-3861 (2005).
Cao, D. et al, "A generalized inverse planning tool for volumetric-modulated arc therapy," Phys. Med. Biol. 54, 6725-6738 (2009).
Chambolle et al, "A first-order primal-dual algorithm for convex problems with applications to imaging," J. Math. Imaging Vision 40, 120-145 (2011).

(Continued)

*Primary Examiner* — David P Porta
*Assistant Examiner* — Fani Boosalis
(74) *Attorney, Agent, or Firm* — Quarles & Brady LLP

(57) ABSTRACT

A system and method are provided for generating and delivering a volumetric modulated arc therapy ("VMAT") plan to a patient. In some aspects, the method includes receiving a representation of a patient comprising information related to target and non-target volumes of interest and generating an objective function based on the representation of the patient. The method also includes performing an iterative optimization process using the objective function to generate a VMAT plan and generating a report according to the VMAT plan.

20 Claims, 7 Drawing Sheets
(5 of 7 Drawing Sheet(s) Filed in Color)

(56) References Cited

OTHER PUBLICATIONS

Cheng, L.-T. et al, "Binary level-set shape optimization model and algorithm for volumetric modulated arc ther-apy in radiotherapy treatment," SIAM J. Sci. Comput. 35, B1321-B1340 (2013).
Condat, L. "A Primal-Dual Splitting Method for Convex Optimization Involving Lipschitzian, Proximable and Linear Composite Terms," Journal of Optimization Theory and Applications 158, 460-479 (2013).
Craft, et al, "Multicriteria VMAT optimization," Med. Phys. 39, 686-696 (2012).
Crooks, et al, "Aperture modulated arc therapy," Phys. Med. Biol. 48, 1333-1344 (2003).
Dong, P. et al, "4pi noncoplanar stereotactic body radiation therapy for centrally located or larger lung tumors," Int. J. Radiat. Oncol., Biol., Phys. 86, 407-413 (2013).
Earl, M., et al, "Inverse planning for intensity-modulated arc therapy using direct aperture optimization," Phys. Med. Biol. 48, 1075-1089 (2003).
Gorski, J., et al, "Biconvex sets and optimization with biconvex functions: A survey and extensions," Math. Methods Oper. Res. 66, 373-407 (2007).
Grégoire et al, "State of the art on dose prescription, reporting and recording in Intensity-Modulated Radiation Therapy (ICRU report No. 83)," Cancer/Radiothér. 15, 555-559 (2011).
Jin, J.-Y., et al, "Advances in treatment techniques: Arc-based and other intensity modulated therapies," Cancer J. 17, 166-176 (2011).
Kawashima, M, et al, "Comparison of total MU and segment areas in VMAT and step-and-shoot IMRT plans," Radiol. Phys. Technol. 6, 14-20 (2013).
Kim, H, et al, "Dose optimization with first-order total-variation minimization for dense angularly sampled and sparse intensity modulated radiation therapy (DASSIM-RT)," Med. Phys. 39, 4316-4327 (2012).
Luan, S. et al. "A new MLC segmentation algorithm/software for step-and-shoot IMRT delivery," Med. Phys. 31, 695-707 (2004).

Men, et al, "An exact approach to direct aperture optimization in IMRT treatment planning," Phys. Med. Biol. 52, 7333-7352 (2007).
Neylon, J., et al, "A nonvoxel-based dose convolution/superposition algorithm optimized for scalable GPU architectures," Med. Phys. 41, 101711 (15pp.) (2014).
Nguyen D, et al, "A novel software and conceptual design of the hardware platform for intensity modulated radiation therapy," Med. Phys. 43, 917-929 (2016).
Nguyen D, et al, "Dose domain regularization of MLC leaf patterns for highly complex IMRT plans," Med. Phys. 42, 1858-1870 (2015).
Osher et al, Level set methods and dynamic implicit surfaces. (Springer Science & Business Media, 2006).
Otto, K. "Volumetric modulated arc therapy: IMRT in a single gantry arc," Med. Phys. 35, 310-317 (2008).
Peng, F., et al, "A new column-generation-based algorithm for VMAT treatment plan optimization," Phys. Med. Biol. 57, 4569-4588 (2012).
Que, W, "Comparison of algorithms for multileaf collimator field segmentation," Med. Phys. 26, 2390-2396 (1999).
Rao, M., et al, "Comparison of Elekta VMAT with helical tomotherapy and fixed field IMRT: Plan quality, delivery efficiency and accuracy," Med. Phys. 37, 1350-1359 (2010).
Salari et al, "A column-generation-based method for multi-criteria direct aperture optimization," Med. Phys. 58, 621-639 (2013).
Shepard D. M., et al., "An arc-sequencing algorithm for intensity modulated arc therapy," Med. Phys. 34, 464-470 (2007).
Verbakel W.F.A.R., et al, "Volumetric intensity-modulated arc therapy vs conventional IMRT in head-and-neck cancer: A comparative planning and dosimetric study," Int. J. Radiat. Oncol., Biol., Phys. 74, 252-259 (2009).
Xia, P, et al. "A leaf sequencing algorithm to enlarge treatment field length in IMRT," Med. Phys. 29, 991-998 (2002).
Yu, C.X., "Intensity-modulated arc therapy with dynamic multileaf collimation: An alternative to tomotherapy," Phys. Med. Biol. 40, 1435-1449 (1995).
Zhu, L. et al, "Using total-variation regularization for intensity modulated radiation therapy inverse planning with field-specific numbers of segments," Physics in medicine and biology 53, 6653 (2008).

* cited by examiner

SYSTEM AND METHOD FOR VOLUMETRIC MODULATED ARC THERAPY

CROSS-REFERENCE TO RELATED APPLICATIONS

This application is based on, claims priority to, and incorporates herein by reference in its entirety U.S. Provisional Application 62/479,296, filed Mar. 30, 2017, and entitled "SYSTEM AND METHOD FOR NON-PROGRESSING SAMPLING IN VOLUMETRIC MODULATED ARC THERAPY."

STATEMENT REGARDING FEDERALLY SPONSORED RESEARCH

This invention was made with government support under R43CA183390 and R01CA1883300 awarded by the National Institutes of Health. The government has certain rights in the invention.

BACKGROUND

The present disclosure generally relates to systems and methods for radiation therapy. More particularly, the present disclosure generally relates to systems and methods for designing radiation treatment plans for radiation therapy.

Volumetric modulated arc therapy ("VMAT") is becoming a widely adopted radiation treatment technique due to its ability to achieve highly conformal dose distributions when treating patients using radiation. The theoretical framework of VMAT is based on an earlier technique known as intensity modulated arc therapy ("IMAT"). In IMAT, radiation dose is delivered inside a targeted volume by directing radiation from a number of angles along a given arc, and using various aperture configurations at each beam angle along the arc. However, to achieve satisfactory dose distributions in a targeted volume using IMAT, multiple arcs were often required. Therefore, more practical algorithms, such as VMAT algorithms, employing one or two arcs were subsequently developed.

Compared to the more traditional static beam intensity modulated radiation therapy ("IMRT"), VMAT is significantly more efficient in both treatment time and total monitor units ("MU") for similar dose distributions. However, unlike IMRT, the arc optimization problem presented by VMAT is significantly more complex, due to the substantially increased number beam orientations and mechanical constraints of the gantry and collimator of the treatment machines.

To avoid the computational complexity for optimization beam configurations in VMAT, several approaches have developed. One example is the multiresolution method, in which a set of sparse beams are first optimized, and new beams are progressively inserted between sparsely sampled beams using interpolation. Then MLC aperture shapes and weights are randomly sampled using simulated annealing. Typically, VMAT often attempts to optimize about 180 or more beams around a patient. The process would then starts with a small set of equally distributed beams, for example, six beams. An inverse optimization is then performed without much computational burden. Once solved, new beams are interpolated and feasible solutions are searched in the vicinity of the previous solutions. The process is then repeated until the desired number of beams is reached. Although this method has been effective in reducing the complexity of the optimization problem, such greedy heuristic methods do not guarantee optimality. In addition, results are often difficult to reproduce and generate inferior dosimetry due to the lack of global optimization. Furthermore, computational burden increases as more beams are added for multiple arcs and non-coplanar arcs.

Despite the potential for using a single arc, in practice, two or more arcs are often utilized with VMAT in order to achieve the desired dosimetry. This is because achieving optimal results often requires applying different initial conditions. Also, in addition to the stochastic nature of simulated annealing, optimization results depend highly on the order and timing in which the parameters, such as weights and penalties, are being applied. As a result, reproducing an existing plan is difficult, if not impossible, and multiple iterations are often required to achieve optimality.

Due to the importance that VMAT plays in today's radiotherapy practice, there is a strong need to overcome the existing limitations of previous technologies.

SUMMARY

The present disclosure overcomes the drawbacks of previous technologies by providing a system and method for generating a radiotherapy treatment for volumetric modulated arc therapy ("VMAT"). In particular, a novel optimization framework is introduced that solves an optimization problem as a global problem. As will be described, in this framework, a single optimization function is utilized that includes a level set function to regularize aperture shapes without relying on a present aperture library. The optimization may then be solved using a proximal-class primal-dual algorithm, which is much more robust than stochastic methods currently available in VMAT solutions.

In accordance with one aspect of the present disclosure, a method for generating a volumetric modulated arc therapy ("VMAT") plan is provided. The method includes receiving a representation of a patient comprising information related to target and non-target volumes of interest, and generating an objective function based on the representation of the patient. The method also includes performing an iterative optimization process using the objective function to generate a VMAT plan, and generating a report according to the VMAT plan.

In accordance with another aspect of the present disclosure, a volumetric modulated arc therapy ("VMAT") system is provided. The system includes a radiation source configured to generate and direct radiation to a patient, and a gantry housing the radiation source and configured to rotate about an axis of rotation. The system also includes a control mechanism configured to control the rotation of the gantry and the delivery of radiation from the radiation source to a target volume in the patient, and a computer in communication with the control mechanism. The computer is configured to receive a representation of a patient comprising information related to target and non-target volumes of interest, and generate an objective function based on the representation of the patient. The computer is also configured to perform an iterative optimization process using the objective function to generate a VMAT plan, generate and provide control signals, corresponding to the VMAT plan, to the control mechanism to irradiate the patient.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Volumetric modulated arc therapy ("VMAT") is a widely employed radiation therapy technique that can achieve dosimetry comparable with static beam intensity modulated radiation therapy ("IMRT") while reducing monitor units and treatment time. Current methods for generating VMAT plans often utilize algorithms that do not guarantee optimality and produce inconsistent results. For instance, the multiresolution method optimizes a set of sparsely selected beam angles, and progressively inserts new beams using interpolation. This greedy heuristic approach does not guarantee optimality, and can produce inferior dosimetry.

To avoid stochastically simulated annealing and direct optimization approach the multiresolution method, one group developed a column-generation-based VMAT algorithm. This iterative technique begins by selecting an aperture for a given beam angle from a set of apertures based on its contribution to an objective function. The optimization then proceeds to the next beam angle in a set of densely sampled arc beams and selects the next aperture, imposing potential mechanical constraints based on the previous aperture. Such greedy heuristic approach is limited, however, in that it solves a sub-problem at each step, and does not simultaneously optimize all possible beam angles. Also, the number of possible aperture shapes increases combinatorially with each iteration. Furthermore, using a complete aperture set (e.g. for a large tumor, or high resolution dose modulation) quickly becomes mathematically intractable.

Another group introduced a binary level-set model in the optimization VMAT. While efficient, the binary level-set is discontinuous, and derivatives at the boundary do not exist, which can lead to poor accuracy. To avoid the progressive sampling issue, yet another group developed an approach that starts with an IMRT optimization every 2° of an arc, and then creates apertures by merging and simplifying adjacent fluence maps. However, this leads to another problem that is common in inverse treatment planning, which is that heuristic conversion from a fluence map to multi-leaf collimator ("MLC") segments typically introduces noticeable and unpredictable dosimetric quality degradations.

As appreciated from the above, VMAT optimization methods to date have a number of drawbacks and produce empirical solutions, which are limited in consistency and quality. Therefore, the present disclosure provides a system and method for generating a radiotherapy treatment for volumetric modulated arc therapy ("VMAT") that overcome the limitations of these previous technologies. Specifically, a novel direct aperture optimization framework is introduced that is non-progressive and provides significantly improved results. Termed herein as comprehensive VMAT ("comVMAT"), the present framework utilizes an optimization function that may include a dose fidelity term, an anisotropic total variation term, and a level set function.

Figure 1:
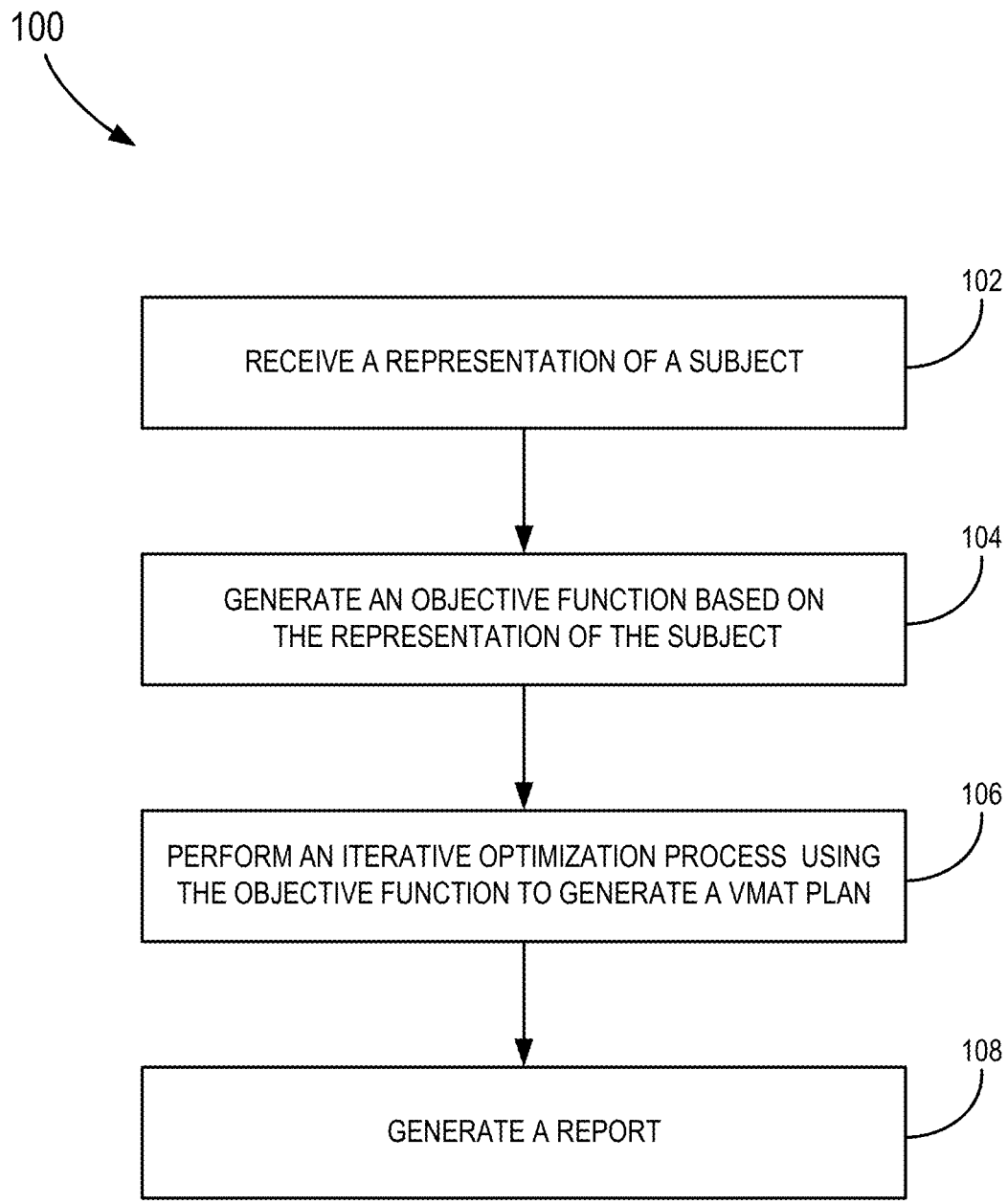
FIG. 1 is a flowchart setting forth steps of a process, in accordance with aspects of the present disclosure.

Referring particularly to FIG. 1, a flowchart setting forth steps of a process 100, in accordance with aspects of the present disclosure, is shown. The process 100, or various steps therein, may be carried out using or in cooperation with any suitable device, apparatus or system, such as the system described with reference to FIG. 6.

In some implementations, steps of the process 100 may be performed using at least one processor configured to execute programming or instructions stored in non-transitory computer readable media. The processor may be a general-purpose processor. Alternatively, the processor may be a dedicated or application-specific processor having non-transitory programming or executable instructions hardwired therein. For example, steps of the process 100 may be carried out using an optimizer or a processing module of a computer.

The process 100 may begin at process block 102 with receiving a representation of a patient. The representation, received from an imaging system, database or data server, may include images, or image data, acquired from a patient, for instance, during a treatment simulation protocol. For example, the images may include computed tomography ("CT") images, magnetic resonance ("MR") images, positron emission tomography ("PET") images, and others. The images may be one-dimensional ("1D"), two-dimensional ("2D"), three-dimensional ("3D") and four-dimensional ("4D") images.

In some aspects, the representation at process block 102 may also include additional information related to target and non-target volumes of interest ("VOI"). This may include contours of diseased and normal tissue structures, as well as dosing requirements or dose constraints based upon predetermined dose prescriptions. Alternatively, a user or clinician may provide such information. For instance, a clinician may select VOIs, either manually or with the help of automated or semi-automated segmentation algorithms, and provide specific dose constraints for the selected VOIs.

Then, an optimization framework may then be applied to generate a VMAT plan. As indicated by process block 104, this includes generating an objective function based the received representation. As discussed in more detail below, the optimization function may include an L2-norm fidelity term that is used to penalize the difference between an optimized dose and a prescribed dose. The optimization function may also include an anisotropic total variation term that can promote piecewise continuity in the fluence maps, and allowing for direct aperture optimization. In addition, a level set function may be further included in the optimization function in order to describe the aperture shapes, with the difference between aperture shapes at adjacent angles being penalized to control multi-leaf collimator ("MLC") motion range.

Then, at process block 106, the objective function may be used in an iterative optimization process that is carried out to generate the VMAT plan. In particular, the VMAT plan may reflect a set of optimized apertures corresponding to various beam angles in an arc used to irradiate the patient, as well as duration of exposure for each aperture. In some implementations, a block minimization algorithm may be adopted to solve the optimization function in the optimization process. An alternating optimization strategy may also be used to solve the fluence intensity and aperture shapes simultaneously.

A report may then be generated based on the VMAT plan generated, as indicated by process block 108. The report may be in any form and include a variety of information, including information describing beam characteristics and delivery configurations optimized using an optimization framework, in accordance with the present disclosure. For example, the report may be provided as output to a display.

In some aspects, report may include instructions suitable for execution by a therapy system, such as the VMAT system described with reference to FIG. 6. For instance, the report may include control signals directing the therapy system to select optimized apertures at specified beam angles in relation to the patient. The control signals may also direct the therapy system to irradiate the patient using the optimized apertures, each aperture irradiating the patient for a specified period of time. The control signals may also direct the therapy system to use the optimized apertures in a specified order to irradiate the patient.

The present optimization framework will now be described. In this framework, an objective function can be generated using the following form:

$$\underset{\{f_\theta, c_\theta, \Phi_\theta\}_{\theta=0}^{n}}{\operatorname{argmin}} \underbrace{\frac{1}{2}\left\|W\left(\sum_\theta (A_\theta f_\theta) - d_0\right)\right\|_2^2}_{\text{dose fidelity term}} + \quad (1)$$

$$\underbrace{\sum_\theta (\lambda_1 \|D_{1\theta} f_\theta\|_1 + \lambda_2 \|D_{2\theta} f_\theta\|_1)}_{\text{term set 1}} +$$

$$\underbrace{\sum_\theta \sum_{x,y} \left(\frac{\gamma}{2}[(f_{\theta xy} - c_\theta)^2 H(\Phi_\theta(x,y)) + f_{\theta xy}^2 (1 - H(\Phi_\theta(x,y)))]\right.}_{\text{term set 2}} +$$

$$\underbrace{\left.\frac{k}{2}[(H(\Phi_\theta(x,y)) - H(\Phi_{\theta-1}(x,y)))^2 + (H(\Phi_\theta(x,y)) - H(\Phi_{\theta+1}(x,y)))^2]\right)}_{\text{term set 3}}$$

patient to $f \geq 0$, where $f_\theta$, $c_\theta$, and $\Phi_\theta$ are the optimization variables. In particular, $f_\theta$ is the vectorized fluence map, $c_\theta$ is a value that f approaches within an aperture, and $\Phi_\theta$ is the level set function, defined as positive where the aperture exists and negative elsewhere. The level set $\{(x,y)|\Phi_\theta(x,y)=0\}$ describes the aperture boundary. Beam angles are indexed by $\theta$, which ranges from 1 to n, and x and y are indices for a beamlet at a given $\theta$. The fluence to dose transformation matrix is denoted by A, and the desired dose, $d_0$, is set as the prescription dose at the PTV and zero elsewhere. The diagonal weighting matrix, W, weighs the structures of interest. The derivative matrices, $D_1$ and $D_2$, take the derivative of the fluence in both directions parallel and orthogonal to the MLC leaf movement. H is the Heaviside function, $$H(v) = \begin{cases} 1 & \text{if } v \geq 0 \\ 0 & \text{if } v < 0 \end{cases}. \quad (2)$$

Essentially, $H(\Phi_\theta(x,y))$ equals one inside the aperture and zero elsewhere. $f_{\theta x,y}$ is a scalar value representing a single beamlet at a given beam angle $\theta$ and an x and y location on the beam, while $f_0$ is a vector of all the fluences at a specific beam angles. $c_0$ is a scalar quantity and only has one value per beam at a given time.

Intuitively, the dose fidelity term, in Eq. (1), attempts to push the final dose as close as possible to the desired dose. Term set 1 is the anisotropic total variation ("TV") regularization, which has been shown to successfully encourage piecewise continuity on the fluence maps. The TV regularization term considers the entire fluence map of the beam, so the term ultimately controls the segment size and shape, abating irregularities and holes in the aperture shape. Soft regulation of the minimal leaf gap and the max leaf interdigitation can be accomplished by independently adjusting the weightings $\lambda_1$ and $\lambda_2$, respectively. Term set 2 is pushing f toward c where the aperture is defined and zero elsewhere. Term set 3 encourages adjacent beam angles to be similar to regulate leaf movement between beam angles. For the first and $n^{th}$ θ, the $\Phi_{\theta-1}(x,y)$ and $\Phi_{\theta+1}(x,y)$ are equal to their respective $\Phi_\theta(x,y)$.

As mentioned, a block minimization algorithm may be used to solve the objective function in Eq. (1). This may be achieved by alternatingly updating the fluence $f_\theta$, aperture intensity $c_\theta$, and aperture shape $\Phi_\theta$, while holding the other two variables constant. The algorithm may be broken down into 3 modules, as described below. Each iteration of the algorithm runs module 1 through 3, and the process is repeated until a satisfactory convergence rate is achieved. Convergence of the alternating approach is assured, as long as each module is able to find a minimum for its respective variable, while holding the other variables constant.

In particular, module 1 minimizes Eq. (1) with respect to $f_\theta$ while holding $c_\theta$ and $\Phi_\theta$ constant. This subproblem can be rewritten as $$\operatorname*{argmin}_{\{f_\theta\}_{\theta=0}^n} \frac{1}{2}\left\|W\left(\sum_\theta (A_\theta f_\theta) - d_0\right)\right\|_2^2 + \sum_\theta (\lambda_1 \|D_{1\theta} f_\theta\|_1 + \lambda_2 \|D_{2\theta} f_\theta\|_1) + \frac{\gamma}{2}\sum_\theta \left(\left\|H_{\Phi_\theta}(f_\theta - c_\theta 1)\right\|_2^2 + \|(I - H_{\Phi_\theta})f_\theta\|_2^2\right), \quad (3)$$

patient to $f \geq 0$, where I is the identity matrix, and $H_{\Phi_\theta}$ in this notation is a diagonal matrix that has the information of $H(\Phi_\theta(x,y))$ along its diagonal for all x and y. Essentially, the diagonal of $H_{\Phi_\theta}$ has a value of 1 if the corresponding $\Phi_\theta(x,y)$ is positive and zero otherwise. The formulation may be solved using the Chambolle-Pock algorithm, a proximal-class primal-dual algorithm. This algorithm solves the optimization problem in the form of $$\text{minimize } S(Kx)+R(x). \quad (4)$$

Here, S and R are lower semicontinuous functions, and K is a matrix. Equation (3) can be written in the form of Eq. (4) by defining the following:

$$K = \begin{bmatrix} WA \\ D_1 \\ D_2 \\ H_\Phi \\ I - H_\Phi \end{bmatrix}, \quad (5)$$

$$A = [A_{\theta=1} \; L \; A_{\theta=n}],$$

$$D_1 = \begin{bmatrix} D_{1\theta=1} & L & 0 \\ M & O & M \\ 0 & L & D_{1\theta=n} \end{bmatrix},$$

$$D_2 = \begin{bmatrix} D_{2\theta=1} & L & 0 \\ M & O & M \\ 0 & L & D_{2\theta=n} \end{bmatrix},$$

$$H_\Phi = \begin{bmatrix} H_{\Phi_{\theta=1}} & L & 0 \\ M & O & M \\ 0 & L & H_{\Phi_{\theta=n}} \end{bmatrix},$$

$$f = \begin{bmatrix} f_{\theta=1} \\ M \\ f_{\theta=n} \end{bmatrix},$$

$$c = \begin{bmatrix} \overline{1}c_{\theta=1} \\ M \\ \overline{1}c_{\theta=n} \end{bmatrix},$$

$$S(Kf) = s_1(WAf) + s_2(D_1 f) + s_3(D_2 f) + s_4(H_\Phi f) + s_5((I - H_\Phi)f),$$

$$R(f) = \begin{cases} 0 & \text{if } f \geq 0 \\ \infty & \text{otherwise} \end{cases},$$

where $$s_1(g_1) = \frac{1}{2}\|g_1 - W\|d_0\|_2^2, \quad (6)$$
$$s_2(g_2) = \lambda \|g_2\|_1,$$
$$s_3(g_3) = \lambda \|g_3\|_1,$$
$$s_4(g_4) = \frac{\gamma}{2}\|g_4 - H_\Phi c\|_2^2,$$
$$s_5(g_5) = \frac{\gamma}{2}\|g_5\|_2^2.$$

The overrelaxed Chambolle-Pock algorithm may be used to solve this formulation, with the iteration:

$$\overline{f}^{n+1} = \operatorname{prox}_{\tau R}(f^n - \tau K^T z^n),$$
$$\overline{z}^{n+1} = \operatorname{prox}_{\sigma S^*}(z^n + \sigma K(2\overline{f}^{n+1} - f^n)),$$
$$f^{n+1} = p\overline{f}^{n+1} + (1-p)f^n,$$
$$z^{n+1} = p\overline{z}^{n+1} + (1-p)z^n. \quad (7)$$

where τ and σ are step sizes that satisfy the constraint $\tau\sigma\|K\|^2 \leq 1$, and p is the overrelaxation parameter ranging from 0 to 2. The operator norm of K is estimated with the power iteration method. The proximity operator, or "proxy" operator, is defined as $$\operatorname{prox}_{th}(x) = \operatorname*{argmin}_u (h(u) + 1/2t\|u - x\|_2^2),$$

and S* is the convex conjugate of S, defined as $$S^*(z) = \sup_y(z^T y - S(y)).$$

Evaluation of these operations yield closed form, low cost calculations for the Chambolle-Pock algorithm, $$prox_{\sigma s_1^*}(z_1^\mu) = \frac{z_1^\mu - \sigma W d_0}{1 + \sigma}, \quad (8)$$

$$prox_{\sigma s_2^*}(z_2^\mu) = P_{\lambda B}(z_2^\mu),$$

$$prox_{\sigma s_3^*}(z_3^\mu) = P_{\lambda B}(z_3^\mu),$$

$$prox_{\sigma s_4^*}(z_4^\mu) = \gamma\left(\frac{z_4^\mu - \sigma H_\Phi c_\theta \overline{1}}{\gamma + \sigma}\right),$$

$$prox_{\sigma s_4^*}(z_5^\mu) = \frac{\gamma z_5^\mu}{\gamma + \sigma},$$

$$prox_{\tau R}(\hat{x}) = P_+(\hat{x}),$$

and a separable sum rule allows for $$prox_{\sigma s^*}\left(\begin{bmatrix} z_1^\mu \\ z_2^\mu \\ z_3^\mu \\ z_4^\mu \\ z_5^\mu \end{bmatrix}\right) = \begin{bmatrix} prox_{\sigma s_1^*} z_1^\mu \\ prox_{\sigma s_2^*} z_2^\mu \\ prox_{\sigma s_3^*} z_3^\mu \\ prox_{\sigma s_4^*} z_4^\mu \\ prox_{\sigma s_5^*} z_5^\mu \end{bmatrix}. \quad (9)$$

With respect to the second module 2, Eq. (1) is minimized with respect to $c_\theta$ while $\Phi_\theta$ and $f_\theta$ are held constant, which is provided by the closed-form solution $$c_\theta = \frac{\sum_{x,y} f_{\theta xy} H(\Phi_\theta(x,y))}{\sum_{x,y} H(\Phi_\theta(x,y))} \text{ for } \theta = 1, \ldots, n. \quad (10)$$

This calculation takes an average of the beamlet intensities that are defined as part of the aperture for each beam angle.

With respect to the second module 3, Eq. (1) is minimized with respect to $\Phi_\theta$ while $f_\theta$ and $c_\theta$ are held constant, $$\underset{\{\Phi_\theta\}_{\theta=0}^n}{\operatorname{argmin}} \sum_\theta \sum_{x,y} \left(\frac{\gamma}{2}[(f_{\theta xy} - c_\theta)^2 H(\Phi_\theta(x,y)) + f_{\theta xy}^2 (1 - H(\Phi_\theta(x,y)))] + \right.$$
$$\left. \frac{k}{2}[(H(\Phi_\theta(x,y)) - H(\Phi_{\theta-1}(x,y)))^2 + \right.$$
$$\left. (H(\Phi_\theta(x,y)) - H(\Phi_{\theta+1}(x,y)))^2]\right) \quad (11)$$

$\Phi_\theta$ is iteratively updated by the expression $$\Phi_\theta^{i+1}(x,y) = \Phi_\theta^i(x,y) + \frac{d\Phi_\theta^i(x,y)}{dt} dt, \quad (12)$$

where $$\frac{d\Phi_\theta(x,y)}{dt}$$

was derived as $$\frac{d\Phi_\theta(x,y)}{dt} = \frac{\gamma}{2}(2c_\theta f_{\theta xy} - c_\theta^2)\delta(\Phi_\theta(x,y))dt + \quad (13)$$
$$k(H(\Phi_{\theta-1}(x,y)) + H(\Phi_{\theta+1}(x,y)) - 2H(\Phi_\theta(x,y)))\delta(\Phi_\theta(x,y))dt.$$

Practically, a sigmoid function and its derivative can be used to approximate the Heaviside and the Dirac delta function, $$H(\Phi) \cong \operatorname{Sigmoid}(q\Phi) = \frac{1}{1 + e^{-q\Phi}}, \quad (14)$$

$$\delta(\Phi) = \frac{dH(\Phi)}{d\Phi} \cong \frac{d\operatorname{Sigmoid}(q\Phi)}{d\Phi} = \frac{qe^{q\Phi}}{(1 + e^{q\Phi})^2},$$

where q is some constant. A larger value of q allows for the sigmoid function to more closely resemble the Heaviside function. The derivation for $$\frac{d\Phi_\theta^i(x,y)}{dt}$$

can be obtained using the following formulation:

$$\sum_\theta \sum_{x,y} \left(\frac{y}{2}[(f_{\theta xy} - c_\theta)^2 H(\Phi_\theta(x,y)) + f_{\theta xy}^2(1 - H(\Phi_\theta(x,y)))] + \right. \quad (15)$$
$$\left. \frac{k}{2}[2H(\Phi_\theta(x,y))^2 - 2(H(\Phi_{\theta-1}(x,y)) + H(\Phi_{\theta+1}(x,y))) \right.$$
$$\left. H(\Phi_\theta(x,y)) + H(\Phi_{\theta-1}(x,y))^2 + H(\Phi_{\theta+1}(x,y))^2]\right).$$

The formulation can be solved using gradient descent, where $\Phi_\theta$ can be updated by the equation. To iteratively determine $\Phi_\theta$, we change $\Phi_\theta$ by a small step $d\Phi_\theta(x,y)/dt$, which changes Eq. (15) to $$\sum_\theta \sum_{x,y} \left(\frac{y}{2}\left[(f_{\theta xy} - c_\theta)^2 H\left(\Phi_\theta(x,y) + \frac{d\Phi_\theta(x,y)}{dt}dt\right) + \right.\right. \quad (16)$$
$$\left.\left. f_{\theta xy}^2 H\left(\Phi_\theta(x,y) + \frac{d\Phi_\theta(x,y)}{dt}dt\right) + f_{\theta xy}^2\right] + \right.$$
$$\left.\frac{k}{2}\left[2H\left(\Phi_\theta(x,y) + \frac{d\Phi_\theta(x,y)}{dt}dt\right)^2 - 2(H(\Phi_{\theta-1}(x,y)) + \right.\right.$$
$$\left.\left. H(\Phi_{\theta+1}(x,y)))H\left(\Phi_\theta(x,y) + \frac{d\Phi_\theta(x,y)}{dt}dt\right) + \right.\right.$$
$$\left.\left. H(\Phi_{\theta-1}(x,y))^2 + H(\Phi_{\theta+1}(x,y))^2\right]\right).$$

The first order Taylor expansion of Eq. (16) is $$\sum_\theta \sum_{x,y} \left(\frac{y}{2}\left[(f_{\theta xy} - c_\theta)^2 H\left((\Phi_\theta(x,y)) + \delta(\Phi_\theta(x,y))\frac{d\Phi_\theta(x,y)}{dt}dt\right) - \right.\right. \quad (17)$$
$$\left.\left. f_{\theta xy}^2\left(H(\Phi_\theta(x,y)) + \delta(\Phi_\theta(x,y))\frac{d\Phi_\theta(x,y)}{dt}dt\right) + f_{\theta xy}^2\right] + \right.$$

-continued $$\frac{k}{2}\Bigl[2\Bigl(H(\Phi_\theta(x,y))^2 + 2H(\Phi_\theta(x,y))\delta(\Phi_\theta(x,y))\frac{d\Phi_\theta(x,y)}{dt}dt\Bigr) +$$

$$2(H(\Phi_{\theta-1}(x,y)) + H(\Phi_{\theta+1}(x,y)))$$

$$\Bigl(H(\Phi_\theta(x,y)) + \delta(\Phi_\theta(x,y))\frac{d\Phi_\theta(x,y)}{dt}dt\Bigr) +$$

$$H(\Phi_{\theta-1}(x,y))^2 + H(\Phi_{\theta+1}(x,y))^2\Bigr]\Bigr).$$

Gathering all of the terms that include $d\Phi_\theta(x,y)/dt$ results in $$\sum_\theta \sum_{x,y} \Bigl(\frac{\gamma}{2}[(f_{\theta xy} - c_\theta)^2 - f_{\theta xy}^2] + \tag{18}$$

$$\frac{k}{2}[4H(\Phi_\theta(x,y)) - 2(H(\Phi_{\theta-1}(x,y)) + H(\Phi_{\theta+1}(x,y)))]\Bigr]$$

$$\delta(\Phi_\theta(x,y))\frac{d\Phi_\theta(x,y)}{dt}dt +$$

$$\frac{\gamma}{2}[(f_{\theta xy}c_\theta)^2 H(\Phi_\theta(x,y)) - f_{\theta xy}^2 H(\Phi_\theta(x,y)) + f_{\theta xy}^2] +$$

$$\frac{k}{2}[2H(\Phi_\theta(x,y))^2 - 2H(\Phi_{\theta-1}(x,y)) + H(\Phi_{\theta+1}(x,y)))$$

$$H(\Phi_\theta(x,y)) + H(\Phi_{\theta-1}(x,y))^2 + H(\Phi_{\theta+1}(x,y))^2].$$

Simplifying Eq. (18) yields $$\sum_\theta \sum_{x,y} [\frac{\gamma}{2}(c_\theta^2 - 2c_\theta f_{\theta xy}) + k(2H(\Phi_\theta(x,y)) - H(\Phi_{\theta-1}(x,y)) - \tag{19}$$

$$H(\Phi_{\theta+1}(x,y)))]\delta(\Phi_\theta(x,y))\frac{d\Phi_\theta(x,y)}{dt}dt +$$

$$\frac{\gamma}{2}[(c_\theta^2 - 2c_\theta f_{\theta xy})H(\Phi_\theta(x,y)) + f_{\theta xy}^2] +$$

$$\frac{k}{2}[(H(\Phi_\theta(x,y)) - H)\Phi_{\theta-1}(x,y)))^2 +$$

$$(H\Phi_\theta(x,y)) - H(\Phi_{\theta+1}(x,y)))^2].$$

The first set of terms that include $d\Phi_\theta(x,y)/dt$ can be rewritten as the inner product $$\sum_\theta \sum_{x,y} [\frac{\gamma}{2}(c_\theta^2 - 2c_\theta f_{\theta xy}) + \tag{20}$$

$$k(2H(\Phi_\theta(x,y)) - H(\Phi_{\theta-1}(x,y)) - H(\Phi_{\theta+1}(x,y)))]\delta(\Phi_\theta(x,y))dt,$$

$$\frac{d\Phi_\theta(x,y)}{dt} + \frac{\gamma}{2}[(c_{\theta 2} - 2c_\theta f_{\theta xy})H(\Phi_\theta(x,y)) + f_{\theta xy}^2] +$$

$$\frac{k}{2}[(H(\Phi_\theta(x,y)) - H(\Phi_{\theta-1}(x,y)))^2 + (H(\Phi_\theta(x,y)) - H(\Phi_{\theta+1}(x,y)))^2].$$

The terms $f_{\theta_x,y}$, $c_\theta$, $\Phi_\theta$, $\Phi_{\theta 1}$, and $\Phi_{\theta+1}$ are treated as constants while solving for $d\Phi_\theta(x,y)/dt$. Hence, only the terms that have $d\Phi_\theta(x,y)/dt$ need to be considered. It is easy to see that the minimizer of Eq. (20) is when $$\frac{d\Phi_\theta(x,y)}{dt} = \frac{\gamma}{2}(2c_\theta f_{\theta xy} - c_\theta^2)\delta(\Phi_\theta(x,y))dt + k(H\Phi_{\theta-1}(x,y)) + \tag{21}$$

$$H(\Phi_{\theta-1}(x,y)) - 2H(\Phi_\theta(x,y)))\delta(\Phi_\theta(x,y))dt.$$

Once the algorithm has converged, and the apertures shapes no longer change, a final polishing step may be taken to ensure superior plan quality. The formulation locks in the solved aperture shapes and solves for the fluence of each beam angle without the aperture regularization constraints, $$\operatorname*{argmin}_b \|W(AFb - d_0)\|_2^2, \tag{22}$$

patient to $b \geq 0$,

The optimization variable, b, contains one intensity value for each beam angle. F is a binary matrix containing all of the aperture information from $H(\Phi_\theta(x,y))$ for all of the beam angles. These two variables are related to the fluence via the equation f=Fb. This optimization can be easily solved with the Chambolle-Pock algorithm. By solving the optimization in Eq. (22) as the last step, only the dose difference is penalized, ensuring that the regularization and aperture constraints are not hindering the final dosimetric outcome.

Although plan delivery time is not explicitly controlled by the objective function in Eqn. (1), it may be indirectly maintained by weights of terms in the objective function. For instance, the total variation term, term set 1, which minimizes the number of deliverable segments, and the aperture similarity term, term set 3, may be selectively controlled to limit the MLC leaf motion between each angle, and hence delivery time. However, a trade-off between plan quality and delivery time would likely be considered since relaxing the weights on these terms to allow more segments and greater changes between apertures will increase treatment time and offset the benefit of using a single arc.

To test the efficacy of the present approach, single arc comVMAT plans were generated for a glioblastoma multiforme ("GBM") case, a lung ("LNG") case, and two head and neck cases—one with three PTVs (H&N3PTV) and one with four PTVs (H&N4PTV). The plans were optimized using an alternating optimization strategy and utilized 180 beams with 2° angular resolution. Other beam numbers of angular resolution may also be possible. The plans were compared against the traditional clinical VMAT ("clnVMAT") plans utilizing two overlapping coplanar arcs for treatment. A summary of prescription doses and PTV volumes for the four patients is summarized in Table I.

TABLE I

Prescription doses and PTV volumes.

| | Prescription dose (Gy) | PTV volume (cc) |
|---|---|---|
| GBM | 25 | 6.23 |
| LNG | 50 | 47.78 |
| H&N$_{3PTV}$ | 54 | 197.54 |
| | 59.4 | 432.56 |
| | 69.96 | 254.98 |
| H&N$_{4PTV}$ | 54 | 58.98 |
| | 60 | 149.32 |
| | 66 | 242.23 |
| | 70 | 175.20 |

As appreciated from description herein, the present framework utilizes a non-greedy algorithm can simultaneously optimize all beams in an arc and directly generate deliverable apertures to generating comVMAT plans. This algorithm can take advantage of a linear accelerator's full digital capability in dose rate and gantry rotation speed modulation. Furthermore, the algorithm generates plans that are superior to those obtained using existing VMAT algorithms.

Specifically, results herein show that the present optimization framework can be used to generate comVMAT plans that can converge within 600 iterations using a block minimization algorithm. In addition, comVMAT plans are able to consistently reduce the dose to all organs-at-risk ("OARs"), as compared to plans obtained using previous techniques. On average, comVMAT plans reduced the max and mean OAR dose by 6.59% and 7.45%, respectively, of the prescription dose. Reductions in max dose and mean dose were as high as 14.5 Gy in the LNG case and 15.3 Gy in the H&N3PTV case. PTV coverages measured by D95 (95% of the PTV dose), D98 (98% of the PTV dose), and D99 (99% of the PTV dose) were within 0.25% of the prescription dose. By comprehensively optimizing all beams, beams with higher intensities may be utilized, resulting in dose distributions that resemble those from static beam IMRT plans with beam orientation optimization.

To evaluate the present framework, a convolution/superposition code was used with a 6 MV x-ray polyenergetic kernel. Beamlet dose was calculated for 180 equally spaced coplanar beam angles around the patient. Beamlet size was chosen to be 0.5×0.5 cm$^2$, and the dose matrix resolution was 0.25×0.25×0.25 cm$^3$. The resulting dose was stored in a dose matrix A for optimization. A 5 cm ring structure was added to the optimization to minimize dose spillage. Plans for each patient were then optimized using the comVMAT algorithm, and W was adjusted until a desirable dose was achieved.

The comVMAT plans were compared to the patients' respective clnVMAT plans. Specifically, the clnVMAT plans were generated on an Eclipse treatment planning system using two superimposing 360° coplanar arcs with 90° collimator rotation. The PTV D95, D98, D99, Dmax, and PTV homogeneity, defined as D95/D5, were evaluated. The Dmax and Dmean for the OARs were also assessed. Max dose was defined as the dose at 2% of the structure volume, D2, which is recommended by the ICRU-83 report.

Figure 2:
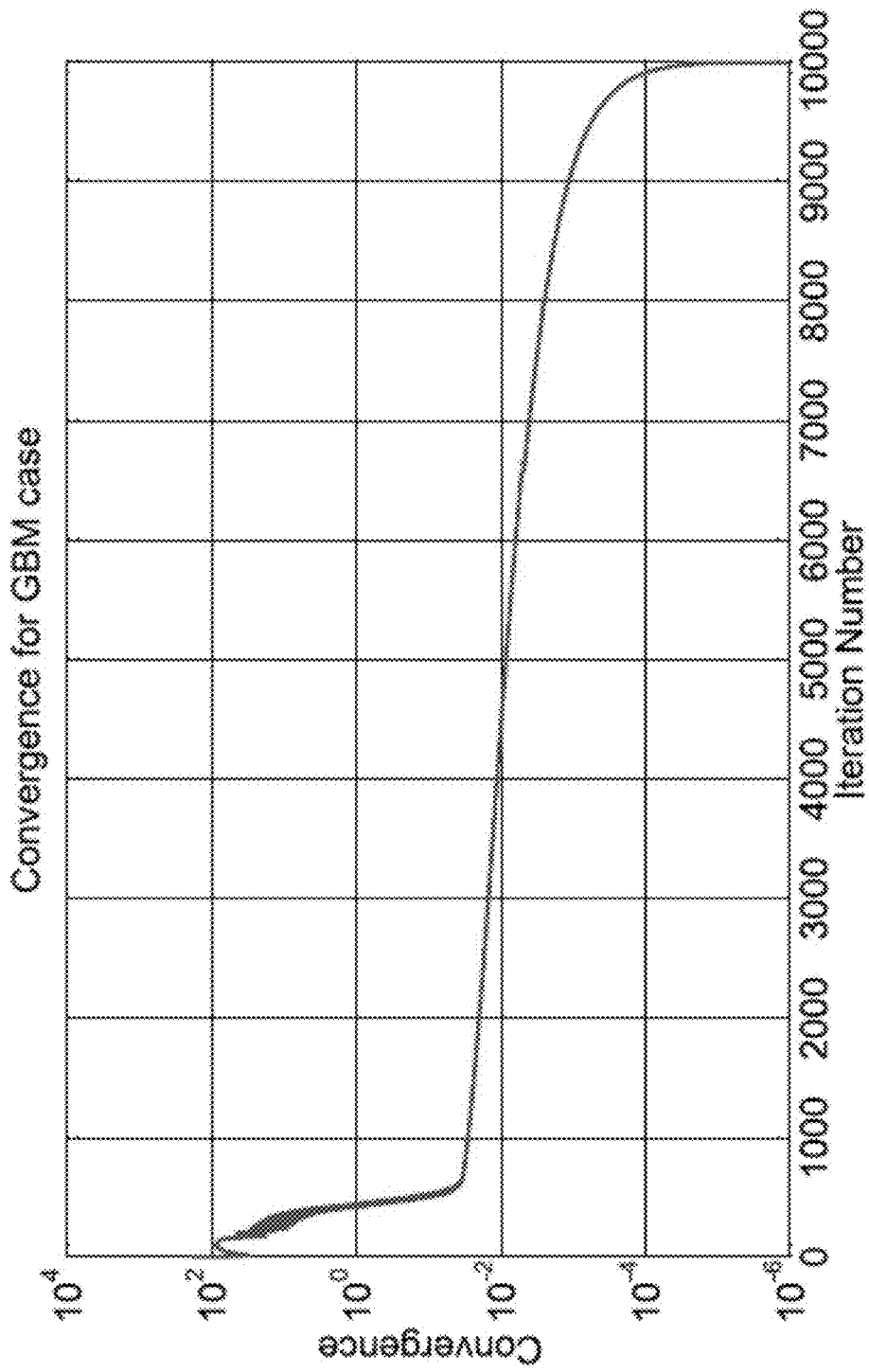
FIG. 2 is graph illustrating the convergence of an objective function for an example glioblastoma multiforme ("GBM") case, in accordance with aspects of the present disclosure.

During optimization of each case, aperture shapes converged within about 600 iterations, with a relative convergence of $10^{-1}$. This degree of convergence has been shown to produce plans that are dosimetrically equivalent to other plans that have tighter convergences. An example convergence plot for the GBM case is shown in FIG. 2, showing the convergence relative to the optimal value taken at the 10,000$^{th}$ iteration. The oscillatory convergence pattern exhibited before about 600 iterations comes from the alternating optimizations solving for f, c, and Φ. During this process, each of the variables were taking small steps toward optimality, which could make the other variables temporarily and slightly less optimal in a given iteration. However, as shown, the oscillatory pattern diminished after about 600 iterations. Depending on various factors—such as case complexity, tumor volume, and body volume—total computational time varied from 5 min for the GBM case to 40 min for the H&N cases, per optimization run. While the overall planning time was within acceptable range, the algorithm was written and tested in MATLAB for proof of principle. Performance could improve considerably using faster programming languages. In addition, unlike prior clinical implementations, no human involvement was required during the optimization process once the weights were set.

Figure 3:
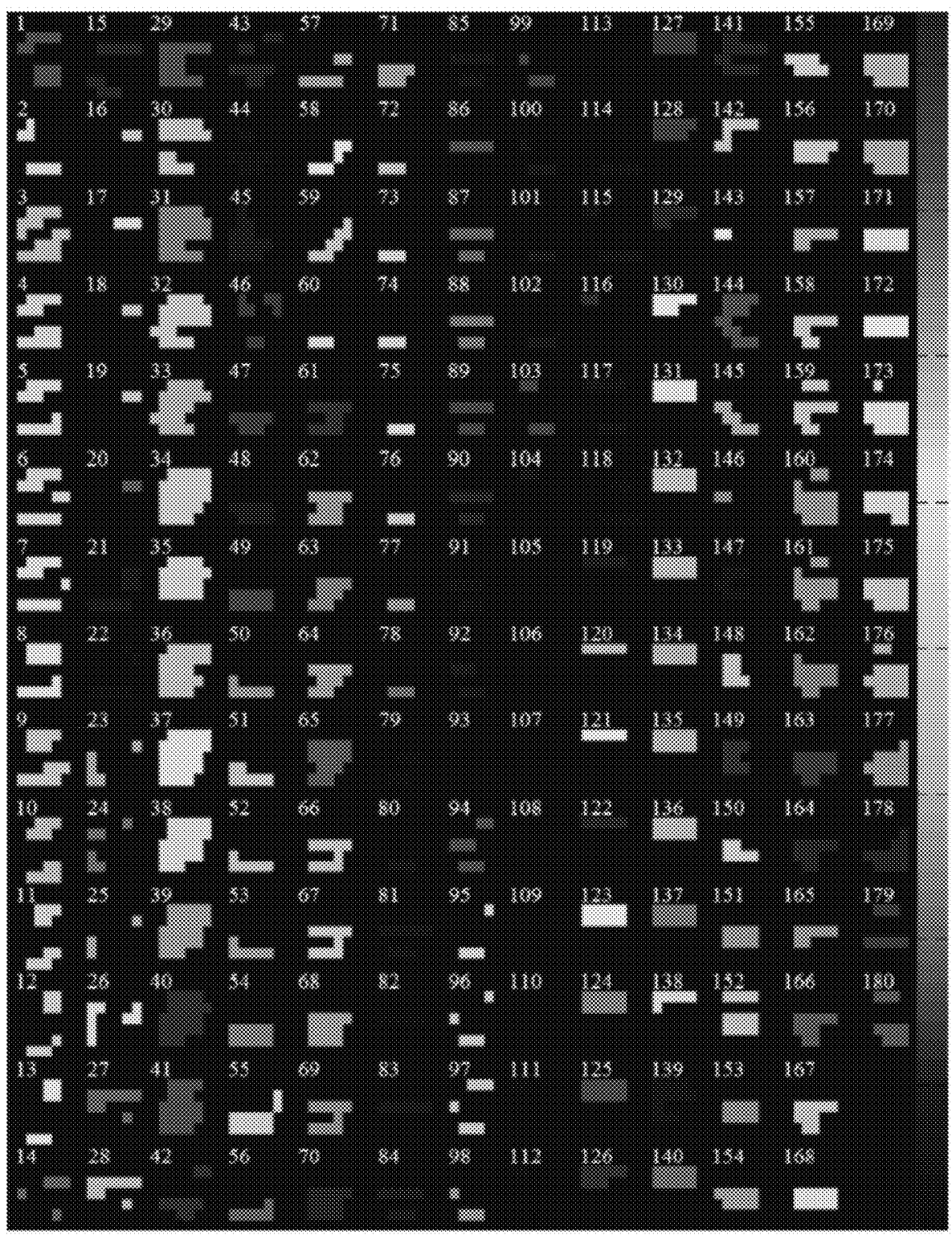
FIG. 3 is a pictorial representation of an example of aperture shapes obtained in accordance with aspects of the present disclosure.
Figure 4A:
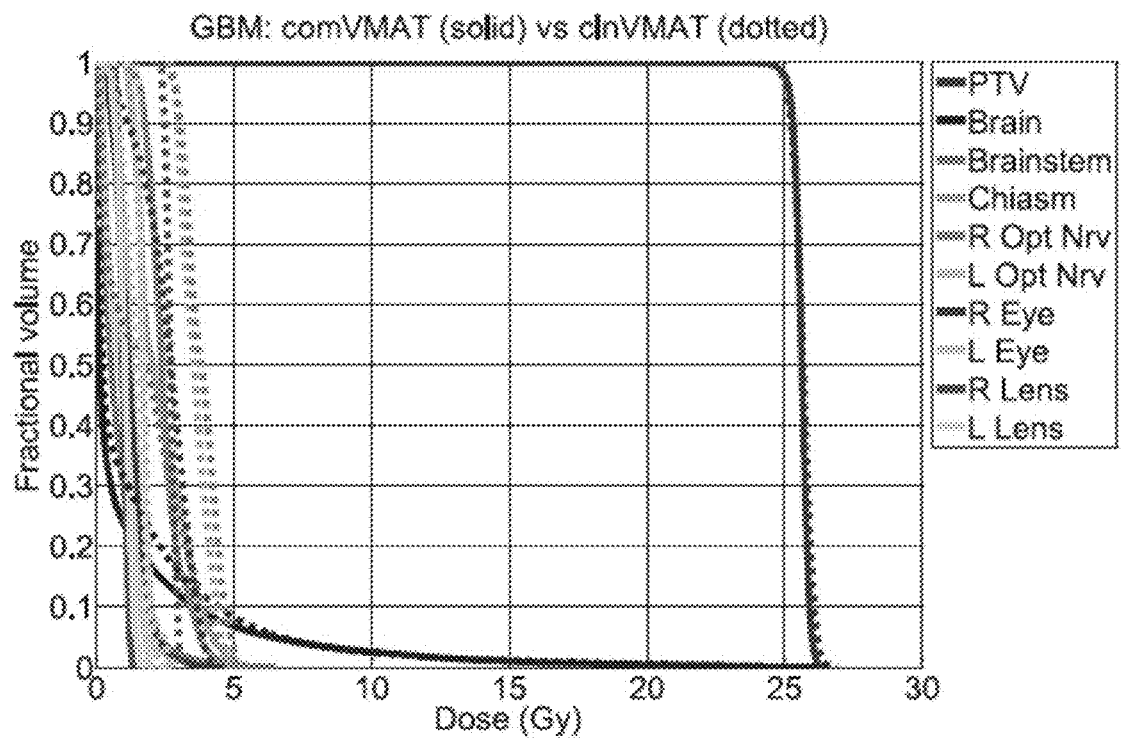
FIG. 4A is a graph showing example dose volume histograms ("DVHs") for a GBM case obtained in accordance with aspects of the present disclosure.
Figure 4B:
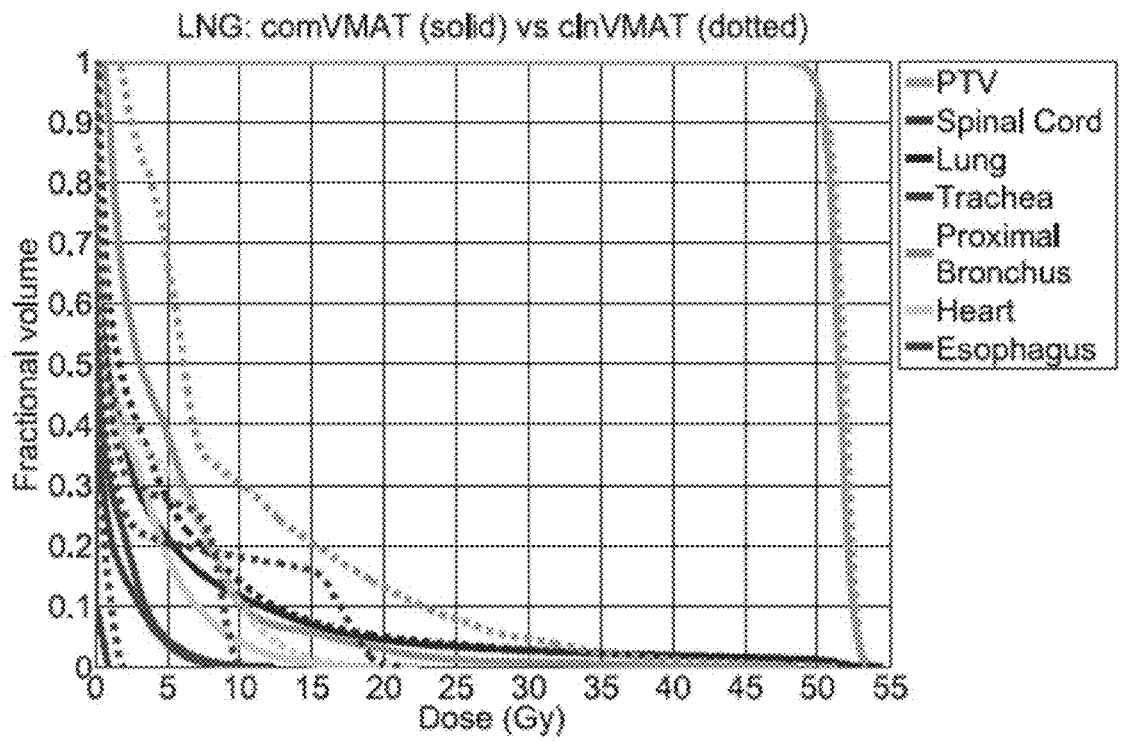
FIG. 4B is a graph showing example DVHs for a lung case obtained in accordance with aspects of the present disclosure.
Figure 4C:
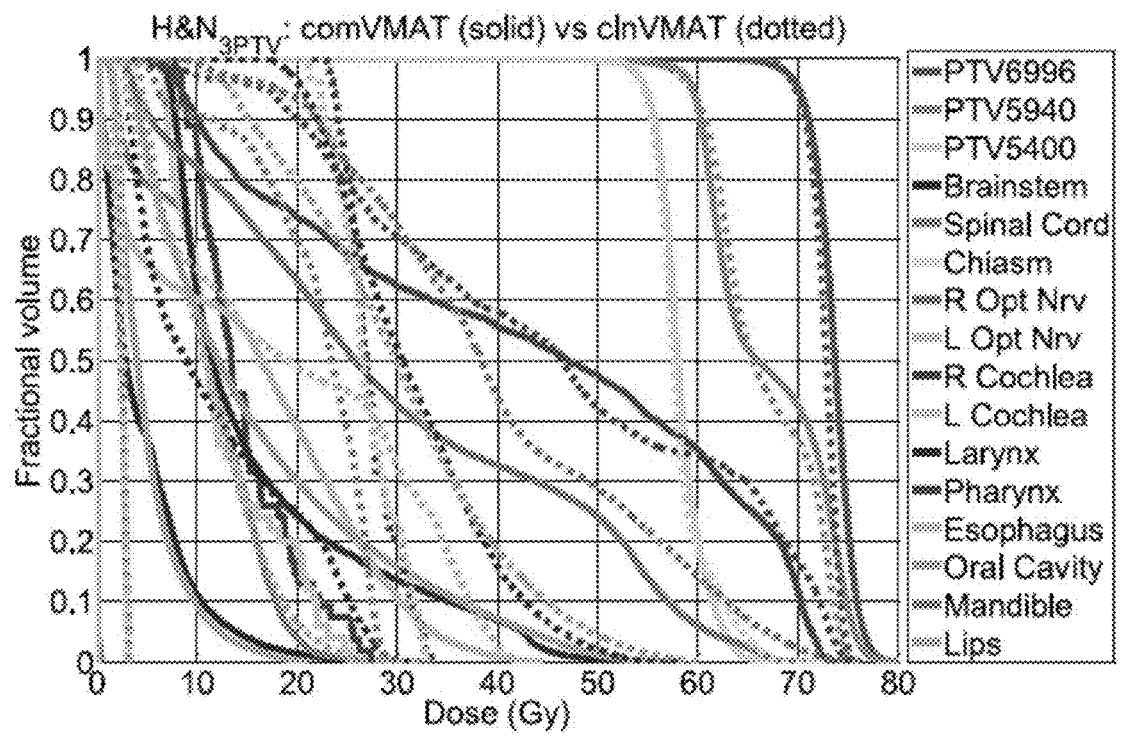
FIG. 4C is a graph comparing example DVHs for a head and neck case obtained in accordance with aspects of the present disclosure.
Figure 4D:
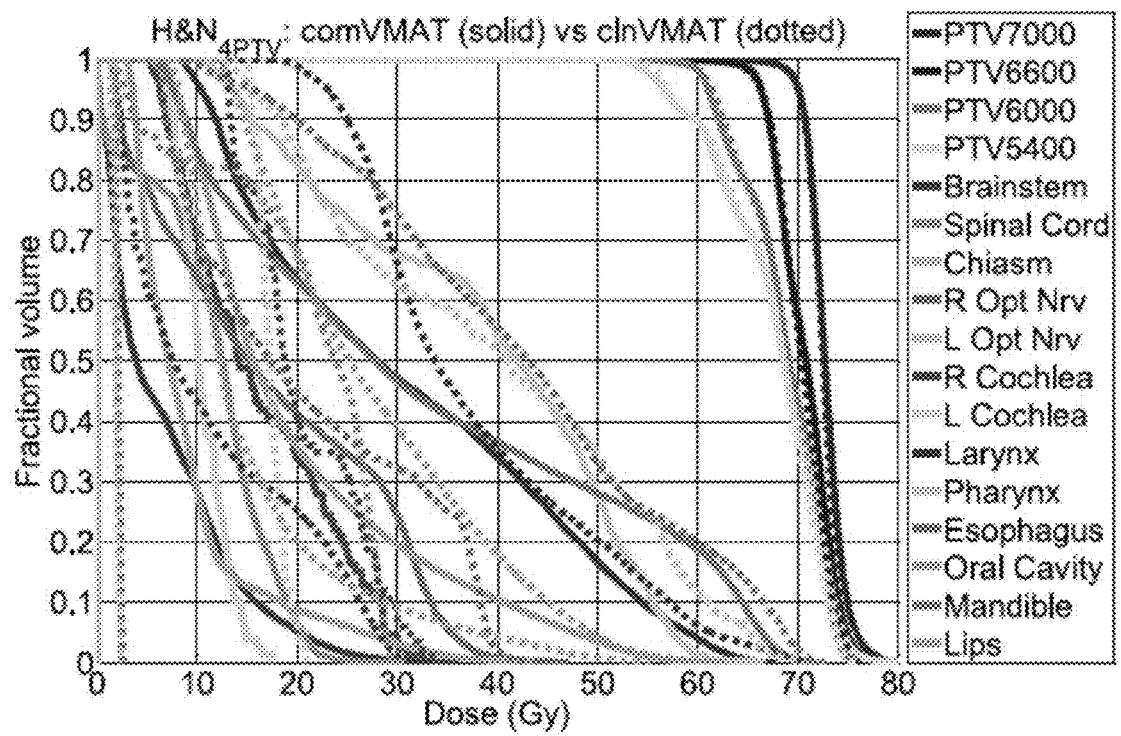
FIG. 4D is another graph comparing example DVHs for a head and neck case obtained in accordance with aspects of the present disclosure.

As mentioned, the comVMAT algorithm was capable of optimizing all 180 beams in the coplanar arc simultaneously for all tested cases. FIG. 3 shows a schematic illustrating the 180 apertures obtained from the GBM case. In the figure, MLC leaf motion is in the horizontal direction. It may be observed that shapes of the beam apertures in the figure are often similar to those of their neighbors. In addition, a small fraction of beams, such as beam 3 and beam 26, require two segments to deliver. That is, delivery of each beam necessitates two MLC configurations. In such cases, delivery of each segment can be accommodated by splitting the beam, which spans 2° in this example, into two beams spanning 1°. In addition, gantry speed may be modulated in order to deliver the apertures.

Referring now to FIGS. 4A-4D, a comparison between comVMAT plans and the clnVMAT plans is shown for each case analyzed. In the figures, dose volume histograms ("DVHs"), representing fractional volume versus dose, are shown for each structure using solid lines (comVMAT) and dotted lines (clnVMAT). As appreciated from the figures, comVMAT demonstrated better OAR sparing while maintaining a competitive PTV dosimetry compared to clnVMAT.

TABLE II

PTV homogeneity, dose coverage (D95, D98, and D99), and Dmax.

| | | PTV statistics | | | | | |
|---|---|---|---|---|---|---|---|
| | | Homogeneity | | D95 | D98 | D99 | Dmax |
| Patient case | | comVMAT | clnVMAT | comVMAT-clnVMAT (Gy) | | | |
| GBM | | 0.968 | 9.958 | +0.08 | +0.09 | +0.02 | −0.21 |
| LNG | | 0.949 | 0.948 | +0.00 | +0.13 | +0.09 | +0.04 |
| H&N$_{3PTV}$ | 54 | 0.874 | 0.847 | +0.23 | +0.19 | +0.06 | −2.30 |
| | 59.4 | 0.786 | 0.801 | +0.02 | +0.73 | +0.15 | +1.96 |
| | 69.96 | 0.915 | 0.935 | +0.29 | −0.12 | −0.63 | +2.36 |
| H&N$_{4PTV}$ | 54 | 0.760 | 0.771 | −0.30 | −0.97 | −1.06 | +1.11 |
| | 60 | 0.818 | 0.832 | −0.40 | −0.18 | −0.11 | +1.17 |
| | 66 | 0.885 | 0.895 | +0.05 | +0.36 | +0.26 | +1.40 |
| | 70 | 0.924 | 0.940 | +0.00 | −0.05 | −0.10 | +2.08 |

The two H&N cases, having multiple PTVs and matching the dose coverage to 95% of the PTVs (FIGS. 4C and 4D), exhibited slightly hotter tails (i.e. a few Gy) to the PTVs compared with the comVMAT plan. However this marginal increase was outweighed by the substantial sparing in all of the OARs for each plan. By contrast, the GBM and LNG cases (FIGS. 4A and 4B), having only one PTV, exhibited superior dosimetry in all aspects of the DVH, as summarized in Table II.

On average, the PTV D95, D98, and D99 changed by −0.01%, +0.02%, and −0.23% of the prescription dose, indicating virtually identical dose coverage between comVMAT and clnVMAT. The average calculations included all of the PTVs from the H&N cases. However, PTV Dmax increased, on average, by 1.40% of the prescription dose. This change was associated to the two H&N cases with multiple PTVs. The GBM case had a reduced max dose to the PTV, while the LNG case minimally increased the PTV max dose by 0.08% of the prescription dose. As summarized in Table III, comVMAT was able to decrease dose for the OARs for all cases, with the largest valued dose differences being negative. Specifically, comVMAT spared the OARs max and mean dose by an average of 6.59% and 7.45% of the prescription dose, respectively. Comparing all the cases, the LNG case had the single largest sparing in max dose for the OARs. Specifically, the proximal bronchus was spared by 14.5 Gy of max dose. Likewise, the single largest reduction in the mean dose to an OAR was achieved in the H&N3PTV case, sparing the larynx by 15.3 Gy of mean dose.

level set function term shaped the fluence to fit the aperture and encouraged the continuity in the aperture shapes between adjacent beams.

Unlike commonly observed solutions utilizing heuristic algorithms, the present optimization framework produces a finalized solution that does not require additional "patches." As described, the Chambolle-Pock algorithm was used to manage optimization, given the size of the optimization problem and that the cost function is not differentiable. This algorithm proved to remarkably fast at solving this type of optimization problem because it did not require solving system of linear equations involving the fluence to dose transformation matrix, A, at every iteration. Unlike first order methods or alternating direction method of multipliers, the Chambolle-Pock algorithm only requires the multiplication of the matrix and its transpose at each iteration, resulting in substantial speedup.

The present framework offers several advantages compared to existing VMAT methods. First, comVMAT optimizes all beam apertures and beam intensities together, providing greater flexibility to reaching targeted or ideal

TABLE III

Largest, smallest, and average values found for (comVMAT-clnVMAT) dose differences for Dmax and Dmean.

| Dose difference comVMAT- clnVMAT (Gy) | Dmax | | | Dmean | | |
|---|---|---|---|---|---|---|
| | Largest value | Smallest value | Average value | Largest value | Smallest value | Average value |
| GBM | −0.02 Chiasm | −1.76 R Lens | −0.80 | −0.43 L Opt Nrv | −1.73 R Lens | −1.04 |
| LNG | −0.38 Long | −14.53 ProxBrench | −5.63 | −0.37 Trachae | −4.61 ProxBrench | −1.98 |
| H&N$_{3PTV}$ | −1.95 Pharyax | −9.74 Brainstem | −4.91 | −2.43 R Opt Nrv | −15.31 Larynx | −8.26 |
| H&N$_{4PTV}$ | −0.56 OralCavity | −13.38 Lips | −4.33 | −1.16 Pharyax | −9.47 Mandible | −5.13 |

Figure 5:
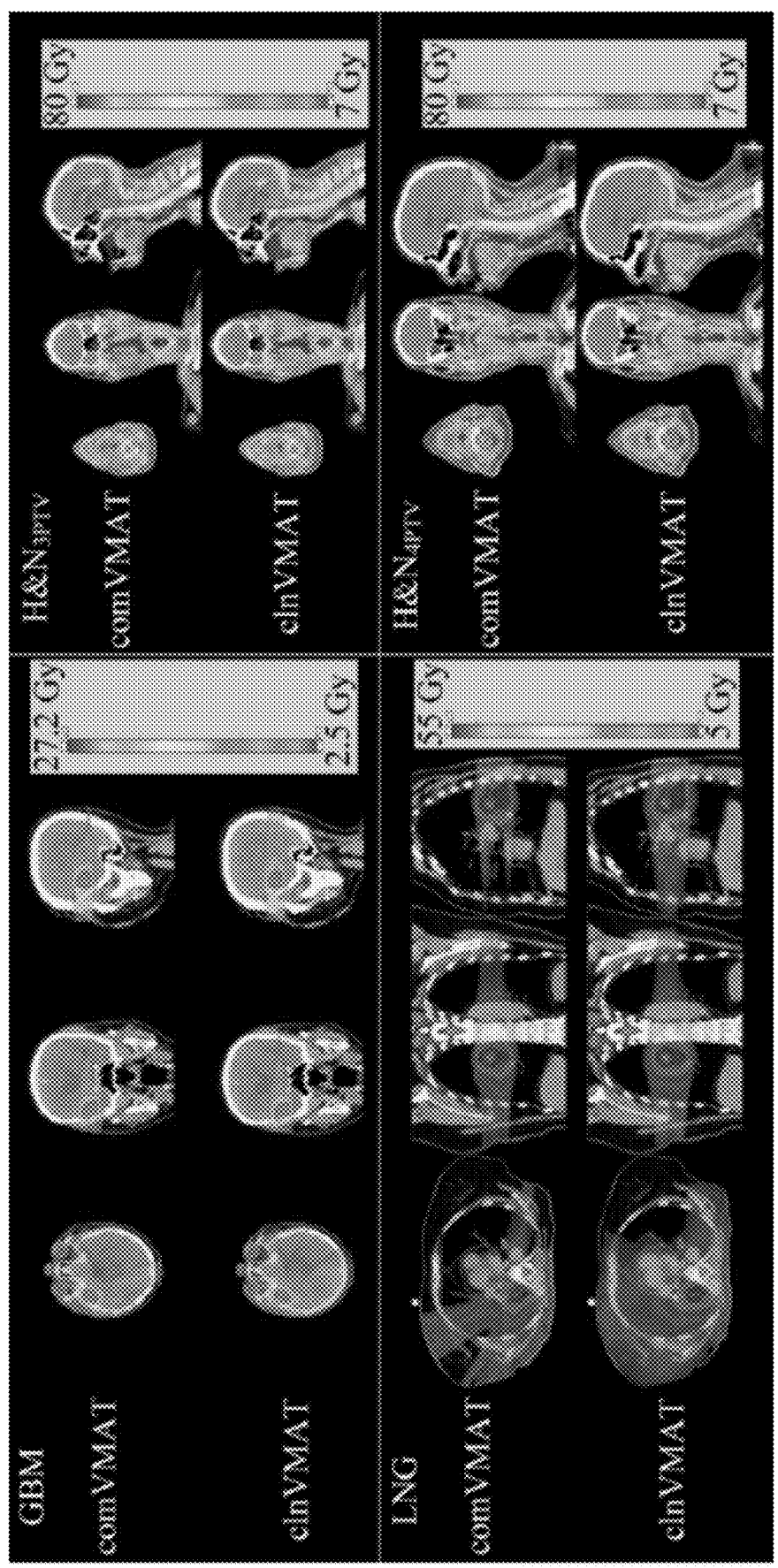
FIG. 5 is a pictorial representation comparing example dose distributions obtained using the present approach relative to previous techniques.

Referring now FIG. 5, the dose distribution achievable using comVMAT is compared with that of clnVMAT. Qualitatively, it may be noted that comVMAT distributes the dose very differently compared clnVMAT. Specifically for the GBM and LNG cases, comVMAT plans gave a much heavier weighting to some selective beams, giving rise to a dose distribution that bears some resemblance to a coplanar IMRT plan, even though there is still only 1 fluence value per beam angle. By contrast, clnVMAT spreads the distribution of fluence intensities more evenly among the beams, giving rise to a less angular modulated dose distribution pattern and greater dose to the OARs. For example, for the GBM plan in FIG. 5, the comVMAT plan was able to entirely avoid the brainstem, while the clnVMAT plan covered the brainstem with at least 2.5 Gy of dose.

In using a proximal-class primal-dual algorithm, such as the Chambolle-Pock algorithm, the present framework, by way of L2-norm fidelity terms and L1-norm regularization terms, introduces fluence map simplification into the dose domain optimization. In addition, the optimization problem can be iteratively solved without greedy heuristic solutions, as implemented by previous technique. This allows all VMAT beams to be optimized at the same time without progressive sampling, providing a number of theoretical and practical advantages.

At the theoretical level, the optimization function introduced herein represents a simple yet complete description of the physical problem. Specifically, an L2-norm fidelity term was used to minimize the dose distribution of the prescription dose, and an anisotropic total variation regularization term was used to piecewise smooth the fluence map. The dosing. For instance, a difference in isodose distribution can be appreciated in FIG. 5, where clnVMAT resulted in a more uniform dose spillage. By contrast, comVMAT gave heavy weights to a narrow range of beams, resulting in dose distribution resembling beam orientation optimized static beam IMRT or hybrid IMRT VMAT plans. In terms of the optimization solver, the analytical solution provided by comVMAT was more robust compared to the stochastic or greedy heuristic algorithms used in existing VMAT methods. Moreover, comVMAT solves the direct aperture problem. By contrast, apertures were obtained in previous methods either from an additional step that degraded the optimization results. Alternatively, apertures were limited to a small subset of available apertures due to nonpolynomial computational cost to include all possible apertures. By contrast, comVMAT can arrive at any aperture shape without being limited to a preset library or the neighborhood of conformal apertures.

As described, the present framework may produce apertures that are deliverable using more than one segment. In the example of FIG. 3, beams 3, 26, and 46 included apertures deliverable using two segments. This is because, while the total variation regularization term in the objective function limits the number of apertures for most beams to 1, there are a small fraction of beams that might require more apertures. Although increasing the regularization weighting may eliminate multiple segments per aperture, there may be a compromise in the dosimetry if the TV penalty is too high. There are multiple solutions in handling the delivery of these particular beams. As described, one approach is to take beams having multi-segment apertures, and split the beams such that each beam delivers a single segment. Alternatively, the two segments may be approximated by the closest single segment. This might change the dose distribution, but such change is expected to be minimal because only a small fraction of beams would need more than one segment.

Multi-segment apertures obtained using the present framework may also provide the opportunity to generate hybrid static beam IMRT and VMAT plans. For instance, by further relaxing the TV regularization, a dosimetric improvement is expected, with more beams needing two or more segments. The gantry speed and LINAC output could then be modulated to deliver these beams, adding more static beam flavor to comVMAT for superior dosimetry.

At the practical level, the single arc comVMAT described herein has been shown to be superior to the current commercial implementation of clnVMAT that uses two superimposing arcs. Also, comVMAT may be potentially advantageous in knowledge based planning because it is more robust to optimization history. By contrast, clnVMAT depends on the entire history of optimization parameter set up, which is impossible to track and incorporate in knowledge based planning. Furthermore, comVMAT plans are reproducible, and provide a single set of optimization parameters for future learning.

In addition, the present formalism does not depend on greedy heuristics and produces dosimetry using a single arc that is at least comparable to the multiple arc VMAT planning techniques. Herein, the dose calculation code was fine-tuned to match the percent depth dose ("PDD") and penumbra of the Eclipse system beams. However, the TPC commissioning process is not entirely transparent in order to achieve an exact reproduction. As such, the present approach may be modified in accordance with specific TPS vendors to achieve an exact comparison.

As appreciated from description herein, a new approach for the comprehensive VMAT optimization was demonstrated. The optimization framework described formulates the VMAT problem using a single optimization function, which includes using a level set function to regularize the MLC aperture shapes without relying on a preset aperture library. The optimization function was solved using a proximal-class primal-dual algorithm, which is more robust than stochastic method used in the existing VMAT solutions. The results showed that the new comVMAT using a single arc was consistently superior in OAR sparing to the clinical VMAT using two arcs, while keeping a similar PTV dosimetry. As a VMAT approach, the particular direct aperture optimization ("DAO") formulation described herein was specifically tailored to produce one segment per beam in most cases. However, the formulation may be generalized using a number of mathematical tools for applications including static beam IMRT may involve multiple levels of segmentation. For instance, it is envisioned that the present approach can be generalized to a libraryless DAO formulation for both static beam and VMAT IMRT problems.

Figure 6:
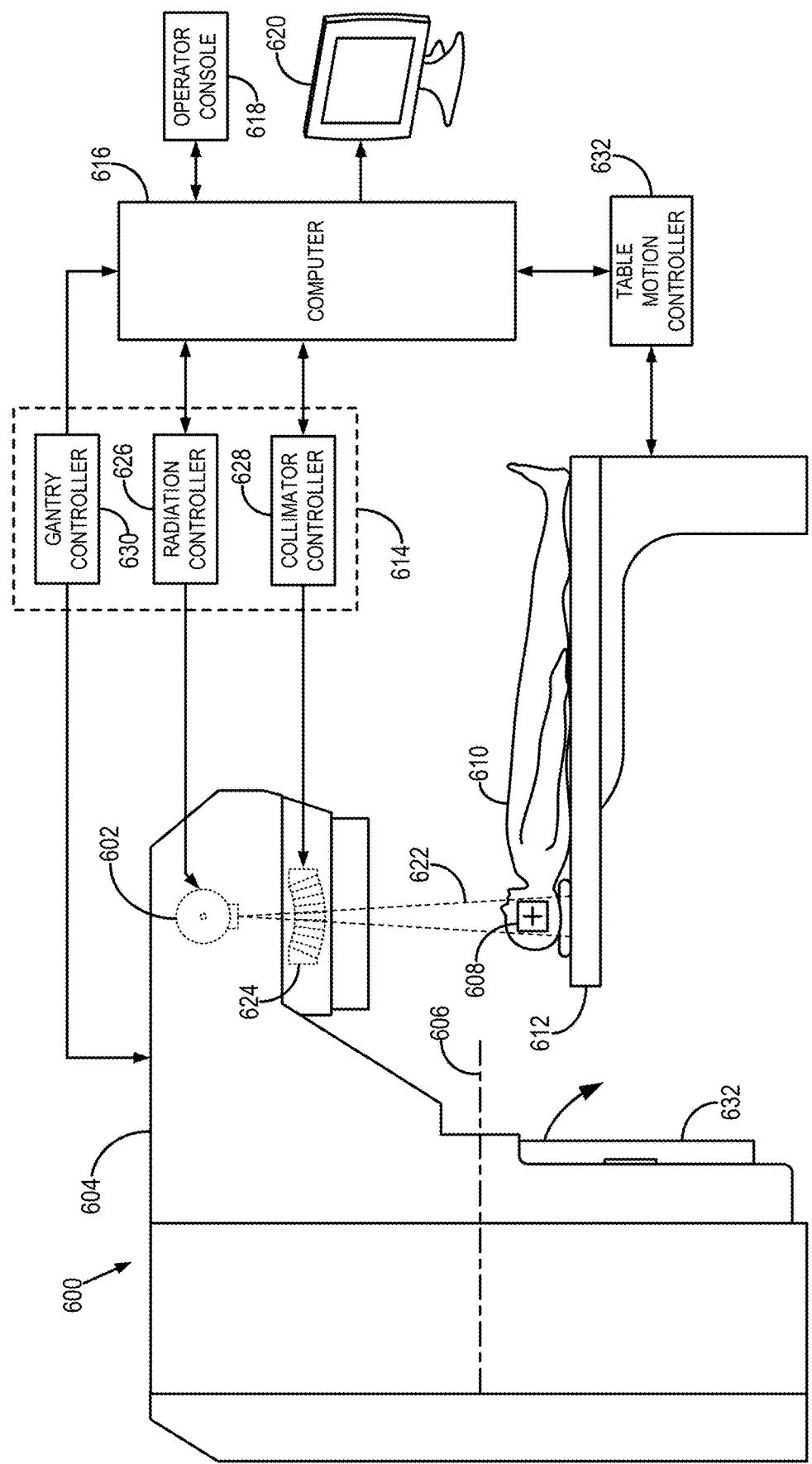
FIG. 6 is a block diagram of an example volumetric modulated arc therapy ("VMAT") system, in accordance with aspects of the present disclosure.

Referring now to FIG. 6, an example of a volumetric modulated arc therapy system 600 that may be used when practicing the present invention. As shown, the system 600 may generally include a radiation source 602, such as an x-ray source or a LINAC. The radiation source 602 is housed at an end of a gantry 604 that rotates about a rotation axis 606. The gantry 604 allows the radiation source 602 to be aligned in a desired manner with respect to a target volume 608 in a patient 610 positioned on a patient table 612. A control mechanism 614 controls the rotation of the gantry 604 and the delivery of radiation from the radiation source 602 to the target volume 608.

The system 600 also include a computer 616 that receives commands and scanning parameters from an operator via a console 618, or from a memory or other suitable storage medium. An associated display 620 allows the operator to observe data from the computer 616, including images or representations of the patient 610 that may be used to review or modify the treatment plan, and to position the patient 610 by way of appropriately adjusting the position of the patient table 612. The operator supplied commands and parameters may also be used by the computer 616 to provide control signals and information to the control mechanism 614.

The radiation source 602 produces a radiation beam 622, or "field," that is modulated by a collimator 624. The collimator 624 may include a multileaf collimator ("MLC") that is composed of a plurality of independently adjustable collimator leaves. In such a configuration, each leaf in the collimator 624 is composed of an appropriate material that inhibits the transmission of radiation, such as a dense radioopaque material, and may include lead, tungsten, cerium, tantalum, or related alloys.

The radiation source 602 mounted on the gantry 604 rotates about a rotation axis 606 so that the radiation beam 622 may irradiate the target volume 608 in the patient 610 from a variety of gantry angles, $\theta_i$. The radiation source 602 is controlled by a radiation controller 626 that forms a part of the control mechanism 614, and which provides power and timing signals to the radiation source 602.

A collimator controller 628, which forms a part of the control mechanism 614, controls the movement of each of the collimator leaves in and out of its corresponding sleeve. The collimator controller 628 moves the collimator leaves rapidly between their open and closed states to adjust the aperture shape of the collimator 624 and, therefore, the shape and fluence of the radiation beam 622. The collimator controller 628 receives instructions from the computer 616 to allow program control of the collimator 624.

A gantry controller 630, which forms a part of the control mechanism 614, provides the signals necessary to rotate the gantry 604 and, hence, to change the position of the radiation source 602 and the gantry angle, $\theta_i$, of the radiation beam 622 for the radiation therapy. The gantry controller 630 connects with the computer 616 so that the gantry 604 may be rotated under computer control, and also to provide the computer 616 with a signals indicating the gantry angle, $\theta_i$, to assist in that control. The position of the patient table 612 may also be adjusted to change the position of the target volume 608 with respect to the radiation source 602 by way of a table motion controller 632, which is in communication with the computer 616.

The system 600 may also include an imager 632 that extends from the gantry 604, which is configured to acquire image data from a patient, for instance, during patient setup. To image the patient, the control mechanism 614 controls the extension of the imager 632 and radiation provided by the radiation source 602. Data acquired by the imager 632 may then be relayed to the computer 616, which then generate images viewable on the display 620. The images may then be used to correct the positioning of the patient prior to treatment.

During operation of the system 600 to deliver treatment, the collimator controller 628 receives, from the computer 616, segmentation information indicating the aperture shape to be used for each gantry angle, $\theta_i$, during each sweep of the radiation source 602, in accordance with the treatment plan. The segmentations describe the intensity of the radiation beam 622 that is desired for each gantry angle, $\theta_i$. The aperture number, shapes and segmentations may be optimized using an optimization framework, as described.

In some aspects, the computer 616 may be configured to generate a VMAT plan using programming or instructions stored in non-transitory computer readable media. To this end, the computer 616 may include an optimizer or a processing module configured specifically to carry out steps for generating the VMAT plan. Alternatively, treatment planning may be performed using an external computer, such as a treatment planning workstation, in communication with the computer 616.

Among other steps, the computer 616 may be configured to receive a representation of a patient using an input, and generate an objective function based on the representation of the patient. As described, the representation may include various images, or image data, acquired from a patient, for instance, during a treatment simulation protocol. To this end, the computer 616 may be configured to control the imager 632 to acquire the imaging data. In addition, as described, the representation received the computer 616 may also include other information, such contours of diseased and normal tissue structures, dosing requirements or dose constraints based upon predetermined dose prescriptions, and so forth.

The computer 616 may then generate an objective function based on the representation of the patient, and generate a VMAT plan by performing an iterative optimization process using the objective function. In some implementations, the VMAT plan generated by the computer 616 may be configured in accordance with the mechanical and operational specifications of the system 600. To this end, the computer 616 may have such information stored in a memory, or may acquire such information from the control mechanism 614 or other system, or may determine such information.

The computer 616 may then report results associated with the VMAT plan generated to a user via the display 620. In addition, the computer 616 may also generate and provide control signals and information to the control mechanism 614 to execute the VMAT plan and treat the patient.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for generating a volumetric modulated arc therapy ("VMAT") plan, the steps of the method comprising:
   receiving a representation of a patient comprising information related to target and non-target volumes of interest;
   generating an objective function based on the representation of the patient;
   performing an iterative optimization process using the objective function to generate a VMAT plan; and
   generating a report according to the VMAT plan.

2. The method of claim 1, wherein the representation comprises at least one image of the patient acquired using at least one of computed tomography ("CT"), magnetic resonance imaging ("MRI"), positron emission tomography ("PET").

3. The method of claim 1, wherein the objective function comprises a dose fidelity term, an anisotropic total variation term, and a level set function term.

4. The method of claim 3, wherein the dose fidelity term is configured to minimize a dose distribution of a prescription dose.

5. The method of claim 3, wherein the anisotropic total variation regularization term is configured to piecewise smooth a fluence of a selected aperture.

6. The method of claim 3, wherein the level set function term is configured to shape a fluence of selected apertures to fit the selected apertures.

7. The method of claim 6, wherein the level set function term is further configured to maintain continuity in aperture shapes between adjacent beams.

8. The method of claim 1, wherein the method further comprises delivering the VMAT plan using a VMAT system.

9. A method for generating a volumetric modulated arc therapy ("VMAT") plan, the steps of the method comprising:
   receiving a representation of a patient comprising information related to target and non-target volumes of interest;
   generating an objective function based on the representation of the patient;
   performing an iterative optimization process using the objective function to generate a VMAT plan;
   generating a report according to the VMAT plan; and
   wherein the method further comprises minimizing the objective function in the iterative optimization process to identify a plurality of apertures each defined by a fluence and an aperture shape.

10. The method of claim 9, wherein the method further comprises applying a proximal-class primal-dual algorithm to minimize the objective function.

11. The method of claim 10, wherein the method further comprises applying a block minimization algorithm to minimize the objective function.

12. A volumetric modulated arc therapy ("VMAT") system comprising:
   a radiation source configured to generate and direct radiation to a patient;
   a gantry housing the radiation source and configured to rotate about an axis of rotation;
   a control mechanism configured to control the rotation of the gantry and the delivery of radiation from the radiation source to a target volume in the patient; and
   a computer in communication with the control mechanism that is configured to:
      receive a representation of a patient comprising information related to target and non-target volumes of interest;
      generate an objective function based on the representation of the patient;
      perform an iterative optimization process using the objective function to generate a VMAT plan; and
      generate and provide control signals, corresponding to the VMAT plan, to the control mechanism to irradiate the patient.

13. The system of claim 12, wherein the representation comprises at least one image of the patient acquired using at least one of computed tomography ("CT"), magnetic resonance imaging ("MRI"), positron emission tomography ("PET").

14. The system of claim 12, wherein the computer is further configured to generate the objective function using a dose fidelity term, an anisotropic total variation term, and a level set function term.

15. The system of claim 14, wherein the dose fidelity term is a L2-norm fidelity term configured to minimize a dose distribution of a prescription dose.

16. The system of claim 14, wherein the anisotropic total variation regularization term is configured to piecewise smooth a fluence of a selected aperture.

17. The system of claim 14, wherein the level set function term is configured to shape a fluence of selected apertures to fit the selected apertures.

18. The system of claim 14, wherein the level set function term is further configured to maintain continuity in aperture shapes between adjacent beams.

19. The system of claim 12, wherein the computer is further configured to minimize the objective function in the iterative optimization process to identify a plurality of apertures each defined by a fluence and an aperture shape.

20. The system of claim 19, wherein the computer is further configured to apply a block minimization algorithm when minimizing the objective function.

* * * * *

UNITED STATES PATENT AND TRADEMARK OFFICE
CERTIFICATE OF CORRECTION

PATENT NO. : 10,857,386 B2
APPLICATION NO. : 15/941112
DATED : December 8, 2020
INVENTOR(S) : Ke Sheng Page 1 of 4

It is certified that error appears in the above-identified patent and that said Letters Patent is hereby corrected as shown below:

In the Specification

Column 6, Lines 23-40, Eq. 1,

"
$$\underset{\{f_\theta, c_\theta, \Phi_\theta\}_{\theta=0}^n}{\text{argmin}} \underbrace{\frac{1}{2}\left\|W\left(\sum_\theta (A_\theta f_\theta) - d_0\right)\right\|_2^2}_{\text{dose fidelity term}} + \sum_\theta \underbrace{\left(\lambda_1 \|D_{1\theta} f_\theta\|_1 + \lambda_2 \|D_{2\theta} f_\theta\|_1\right)}_{\text{term set 1}}$$

$$+ \sum_\theta \sum_{x,y} \underbrace{\left(\frac{\gamma}{2}\left[(f_{\theta xy} - c_\theta)^2 H(\Phi_\theta(x,y)) + f_{\theta xy}^2 (1 - H(\Phi_\theta(x,y)))\right] + \right.}_{\text{term set 2}}$$

$$\underbrace{\left. \frac{k}{2}\left[(H(\Phi_\theta(x,y)) - H(\Phi_{\theta-1}(x,y)))^2 + (H(\Phi_\theta(x,y)) - H(\Phi_{\theta+1}(x,y)))^2\right]\right)}_{\text{term set 3}},$$
"

should be

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*

CERTIFICATE OF CORRECTION (continued)
U.S. Pat. No. 10,857,386 B2

Column 7, Line 45, Eq. 3, "
$$\underset{\{f_\theta, c_\theta, \Phi_\theta\}_{\theta=0}^n}{\operatorname{argmin}} \underbrace{\frac{1}{2}\left\|W\left(\sum_\theta (A_\theta f_\theta) - d_0\right)\right\|_2^2}_{\text{dose fidelity term}} + \underbrace{\sum_\theta \left(\lambda_1 \|D_{1\theta} f_\theta\|_1 + \lambda_2 \|D_{2\theta} f_\theta\|_1\right)}_{\text{term set 1}}$$
$$+ \sum_\theta \sum_{x,y} \left( \underbrace{\frac{\gamma}{2}\left[(f_{\theta xy} - c_\theta)^2 H(\Phi_\theta(x,y)) + f_{\theta xy}^2 (1 - H(\Phi_\theta(x,y)))\right]}_{\text{term set 2}} \right.$$
$$\left. + \underbrace{\frac{k}{2}\left[(H(\Phi_\theta(x,y)) - H(\Phi_{\theta-1}(x,y)))^2 + (H(\Phi_\theta(x,y)) - H(\Phi_{\theta+1}(x,y)))^2\right]}_{\text{term set 3}} \right),$$

should be --
$$\underset{\{f_\theta\}_{\theta=0}^n}{\operatorname{argmin}} \frac{1}{2}\left\|W\left(\sum_\theta (A_\theta f_\theta) - d_0\right)\right\|_2^2 + \sum_\theta \left(\lambda_1 \|D_{1\theta} f_\theta\|_1 + \lambda_2 \|D_{2\theta} f_\theta\|_1\right) +$$
$$\frac{\gamma}{2}\sum_\theta \left(\left\|H_{\Phi_\theta}\left(f_\theta - c_\theta \overset{v}{1}\right)\right\|_2^2 + \left\|(I - H_{\Phi_\theta})f_\theta\right\|_2^2\right),$$
--.

"
$$\underset{\{f_\theta\}_{\theta=0}^n}{\operatorname{argmin}} \frac{1}{2}\left\|W\left(\sum_\theta (A_\theta f_\theta) - d_0\right)\right\|_2^2 + \sum_\theta \left(\lambda_1 \|D_{1\theta} f_\theta\|_1 + \lambda_2 \|D_{2\theta} f_\theta\|_1\right)$$
$$+\frac{\gamma}{2}\sum_\theta \left(\left\|H_{\Phi_\theta}\left(f_\theta - c_\theta \vec{1}\right)\right\|_2^2 + \left\|(I - H_{\Phi_\theta})f_\theta\right\|_2^2\right),$$
--.

Column 8, Line 7, Eq. 5, "$A = [A_{\theta=1} \quad L \quad A_{\theta=n}]$," should be --$A = [A_{\theta=1} \quad \cdots \quad A_{\theta=n}]$,--.

Column 8, Line 10, Eq. 5, "$D_1 = \begin{bmatrix} D_{1\theta=1} & L & 0 \\ M & O & M \\ 0 & L & D_{1\theta=n} \end{bmatrix}$," should be --$D_1 = \begin{bmatrix} D_{1\theta=1} & \cdots & 0 \\ \vdots & \ddots & \vdots \\ 0 & \cdots & D_{1\theta=n} \end{bmatrix}$,--.

Column 8, Line 14, Eq. 5, "$D_2 = \begin{bmatrix} D_{2\theta=1} & L & 0 \\ M & O & M \\ 0 & L & D_{2\theta=n} \end{bmatrix}$," should be --$D_2 = \begin{bmatrix} D_{2\theta=1} & \cdots & 0 \\ \vdots & \ddots & \vdots \\ 0 & \cdots & D_{2\theta=n} \end{bmatrix}$,--.

Column 8, Line 17, Eq. 5, "$H_\Phi = \begin{bmatrix} H_{\Phi_{\theta=1}} & L & 0 \\ M & O & M \\ 0 & L & H_{\Phi_{\theta=n}} \end{bmatrix}$," should be --$H_\Phi = \begin{bmatrix} H_{\Phi_{\theta=1}} & \cdots & 0 \\ \vdots & \ddots & \vdots \\ 0 & \cdots & H_{\Phi_{\theta=n}} \end{bmatrix}$,--.

CERTIFICATE OF CORRECTION (continued)
U.S. Pat. No. 10,857,386 B2

Column 8, Line 21, Eq. 5, "$f = \begin{bmatrix} f_{\theta=1} \\ M \\ f_{\theta=n} \end{bmatrix}$" should be -- $f = \begin{bmatrix} f_{\theta=1} \\ \vdots \\ f_{\theta=n} \end{bmatrix}$ --.

Column 8, Line 26, Eq. 5, "$c = \begin{bmatrix} \overline{1}c_{\theta=1} \\ M \\ \overline{1}c_{\theta=n} \end{bmatrix}$," should be -- $c = \begin{bmatrix} \overline{1}c_{\theta=1} \\ \vdots \\ \overline{1}c_{\theta=n} \end{bmatrix}$, --.

Column 9, Eq. 8, "
$$prox_{\sigma s_1^*}(z_1^\mu) = \frac{z_1^\mu - \sigma W d_0}{1+\sigma},$$
$$prox_{\sigma s_2^*}(z_2^\mu) = P_{\lambda B}(z_2^\mu),$$
$$prox_{\sigma s_3^*}(z_3^\mu) = P_{\lambda B}(z_3^\mu),$$
$$prox_{\sigma s_4^*}(z_4^\mu) = \gamma \left( \frac{z_4^\mu - \sigma H_\Phi c_\theta \overline{1}}{\gamma + \sigma} \right),$$
$$prox_{\sigma s_4^*}(z_5^\mu) = \frac{\gamma z_5^\mu}{\gamma + \sigma},$$
$$prox_{\tau R}(\hat{x}) = P_+(\hat{x}),$$
" should be --
$$prox_{\sigma s_1^*}(\widehat{z_1}) = \frac{\widehat{z_1} - \sigma W d_0}{1+\sigma},$$
$$prox_{\sigma s_2^*}(\widehat{z_2}) = P_{\lambda B}(\widehat{z_2}),$$
$$prox_{\sigma s_3^*}(\widehat{z_3}) = P_{\lambda B}(\widehat{z_3}),$$
$$prox_{\sigma s_4^*}(\widehat{z_4}) = \gamma \left( \frac{\widehat{z_4} - \sigma H_\Phi c_\theta \overline{1}}{\gamma + \sigma} \right),$$
$$prox_{\sigma s_4^*}(\widehat{z_5}) = \frac{\gamma \widehat{z_5}}{\gamma + \sigma},$$
$$prox_{\tau R}(\hat{x}) = P_+(\hat{x}),$$
--.

CERTIFICATE OF CORRECTION (continued)
U.S. Pat. No. 10,857,386 B2

Column 9, Eq. 9, " $prox_{\sigma S^*}\left(\begin{bmatrix} z_1^\mu \\ z_2^\mu \\ z_3^\mu \\ z_4^\mu \\ z_5^\mu \end{bmatrix}\right) = \begin{bmatrix} prox_{\sigma_{S1}^*} z_1^\mu \\ prox_{\sigma_{S2}^*} z_2^\mu \\ prox_{\sigma_{S3}^*} z_3^\mu \\ prox_{\sigma_{S4}^*} z_4^\mu \\ prox_{\sigma_{S5}^*} z_5^\mu \end{bmatrix}.$ " should be -- $prox_{\sigma S^*}\left(\begin{bmatrix} \hat{z}_1 \\ \hat{z}_2 \\ \hat{z}_3 \\ \hat{z}_4 \\ \hat{z}_5 \end{bmatrix}\right) = \begin{bmatrix} prox_{\sigma_{S_1}^*} \hat{z}_1 \\ prox_{\sigma_{S_2}^*} \hat{z}_2 \\ prox_{\sigma_{S_3}^*} \hat{z}_3 \\ prox_{\sigma_{S_4}^*} \hat{z}_4 \\ prox_{\sigma_{S_5}^*} \hat{z}_5 \end{bmatrix}.$ --.